United States Patent [19]
Roberts

[11] Patent Number: 6,124,521
[45] Date of Patent: Sep. 26, 2000

[54] DERMAL WOUND WINDOW DRESSING SECUREMENT SYSTEM

[75] Inventor: Jerry H. Roberts, Okemos, Mich.

[73] Assignee: Tri-State Hospital Supply Corporation, Howell, Mich.

[21] Appl. No.: 09/266,102

[22] Filed: Mar. 10, 1999

[51] Int. Cl.$^7$ .............................. A61F 13/00; A61M 25/02
[52] U.S. Cl. ................................ 602/54; 602/42; 602/56; 604/180
[58] Field of Search ................ 602/41–59; 604/174, 604/177, 179, 180; 606/213, 214, 215, 216; 128/889

[56] References Cited

U.S. PATENT DOCUMENTS

| | | | |
|---|---|---|---|
| 4,275,721 | 6/1981 | Olson | 604/180 |
| 4,490,141 | 12/1984 | Laco et al. | 604/180 |
| 4,641,643 | 2/1987 | Greer | 604/180 |
| 4,941,882 | 7/1990 | Ward et al. | 604/180 |
| 5,035,687 | 7/1991 | Sandbank | 604/180 |
| 5,372,589 | 12/1994 | Davis | 604/180 |
| 5,380,294 | 1/1995 | Persson | 604/180 |
| 5,447,492 | 9/1995 | Cartmell | 602/58 |
| 5,520,629 | 5/1996 | Heinecke et al. | 602/57 |
| 5,685,859 | 11/1997 | Kornerup | 604/180 |
| 5,707,348 | 1/1998 | Krogh | 602/41 |
| 5,833,665 | 11/1998 | Bootman | 604/180 |
| 5,885,254 | 3/1999 | Matyas | 604/180 |
| 5,947,931 | 9/1999 | Bierman | 604/180 |
| 5,968,000 | 10/1999 | Harrison | 602/41 |

*Primary Examiner*—Kim M. Lee
*Attorney, Agent, or Firm*—Fildes & Outland, P.C.

[57] ABSTRACT

A self adherent dermal wound window dressing for the protection of an indwelling catheter access site, providing absorbency, visualization and securement of an indwelling catheter, includes a fabric tape layer having an adhesive side and an opposite non-adhesive side. The fabric tape layer has an opening therein to allow viewing therethrough. A semi-permeable transparent film layer closes the opening in the fabric tape layer and has an adhesive side and an opposite non-adhesive side. The film layer adhesive side is adhered on the non-adhesive side of the fabric layer around the opening. An absorbent fiber layer has an opening generally corresponding to the opening in the fabric tape layer. The fiber layer is mounted on the adhesive side of the fabric tape layer such that the openings in the absorbent fiber and fabric tape layers are in alignment and the fabric tape layer extends beyond the periphery of the absorbent fiber layer. A non-adherent porous film layer of a shape generally corresponding to the shape of the absorbent fiber layer has an adhesive side and an opposite non-adhesive side and is adhered to the absorbent fiber layer by the adhesive side of the non-adherent porous film layer. A latent cut in the fabric tape layer extending beyond the periphery of the absorbent fiber layer receives a catheter tube extending from under the dressing and the fabric tape layer seals the window dressing from contamination around the catheter tube.

13 Claims, 3 Drawing Sheets

DERMAL WOUND WINDOW DRESSING SECUREMENT SYSTEM

FIELD OF THE INVENTION

This invention relates to dermal wound window dressings for the protection of indwelling catheter access sites, and the visualization and securement of the indwelling catheter and more particularly to a self adherent window dressing having a securement system for edge sealing around the indwelling catheter where the catheter tube extends from under the dressing.

BACKGROUND OF THE INVENTION

It is known in the art relating to dressings for indwelling catheter access sites to use self-adherent protective bandage tape or clear film product alternatives that use non-sensitizing hypoallergenic adhesives to cover all or part of the indwelling catheter access sites. Some dressings combine non-woven tape and absorbent gauze-like materials which have skin-mating surfaces of non-adherent film to reduce the effect of adhesive stripping caused by the dressing removal. The absorbency and bacterial barrier of the pad typically varies minimally from one manufacturer to another, but this type of dressing is least occlusive to moisture vapor.

One known dressing system includes an opaque pad for adhesive placement over an access site and an adhesive strip, for adhesive securement to the skin of a patient under a catheter tube as it emerges from underneath the pad, and between the skin and the pad along the edges of the pad in opposite directions from the tube exit location.

While providing a more sterile, reliable and uniform dressing for a vascular access site, the system does not allow the access site to be viewed without removal of the opaque pad and the underneath of the pad is open to contamination around the edges of the catheter tube emerging from the opaque pad and adjacent the opaque pad.

The need exists for a dermal wound window dressing for the protection of indwelling catheter access sites, which provides simultaneous absorbency of moisture, visualization of the skin/cannula exit point and mechanical securement of the indwelling catheter having a securement system for edge sealing around the indwelling catheter where the catheter tube extends from under the dressing.

SUMMARY OF THE INVENTION

The present invention provides a self adherent window dressing having an absorbent pad dressing surrounding a semipermeable transparent cover permitting visual inspection of an indwelling catheter access site; moisture vapor (gaseous) or fluid wicking around the site; and circumfluent absorption of fluid around the site. The window dressing includes a securement system for edge sealing the window dressing around the indwelling catheter where the catheter tube extends from under the dressing next to the skin preventing undesired contaminants from accessing under the dressing from adjacent the catheter tube.

More specifically, the present invention is a self adherent window dressing for the protection of an indwelling catheter access site, providing absorbency, visualization and securement of an indwelling catheter, including a fabric tape layer having an adhesive side and an opposite non-adhesive side. The fabric tape layer has an opening therein to allow viewing therethrough. A semipermeable transparent film layer closes the opening in the fabric tape layer and has an adhesive side and an opposite non-adhesive side. The film layer adhesive side is adhered on the non-adhesive side of the fabric layer around the opening.

An absorbent fiber layer having an opening generally corresponding to the opening in the fabric tape layer is mounted on the adhesive side of the fabric tape layer such that the openings in the absorbent fiber and fabric tape layers are in alignment and the fabric tape layer extends beyond the periphery of the absorbent fiber layer. A non-adherent porous film layer of a shape generally corresponding to the shape of the absorbent fiber layer has an adhesive side and an opposite non-adhesive side and is adhered to the absorbent fiber layer by the adhesive side of the non-adherent porous film layer. A latent cut in the fabric tape layer extending beyond the periphery of the absorbent fiber layer receives a catheter tube extending from under the dressing and the fabric tape layer seals the window dressing from contamination around the catheter tube.

In one embodiment of the invention the cut extends inwardly from the edge of the fabric tape layer and is interrupted by connecting portions which hold the edge of the fabric tape layer adjacent the cut together. Upon application for use, the connecting portions separate to allow the edge of the fabric tape layer to form an occlusive seal by stretching and conforming into the shape of an overt notch around the catheter tube extending from under the dressing.

In another embodiment of the invention, the cut is an indentation extending inwardly from the edge of the fabric tape layer having a V-shape or a U-shape of fabric tape overtly removed to allow the edge of the fabric tape layer to form an occlusive seal by stretching and conforming into the shape of a notch around the catheter tube extending from under the dressing.

In yet another embodiment of the invention, the fabric tape layer extending beyond the absorbent fiber layer periphery includes a line of perforation allowing a separable portion of the fabric tape layer to be separated from a dressing portion of the window dressing. In this embodiment, one or both portions of the separated fabric tape layer include a latent cut extending inwardly from an edge thereof. These cuts are aligned when the dressing is applied allowing for adhesive securement of the separable portion to the skin of a patient under a catheter tube as it emerges from underneath the dressing with the tube received by the cuts, and between the skin and dressing portion along the edges thereof in opposite directions from the tube exit location.

These and other features and advantages of the invention will be more fully understood from the following detailed description of the invention taken together with the accompanying drawings.

DETAILED DESCRIPTION OF THE INVENTION

Figure 1:
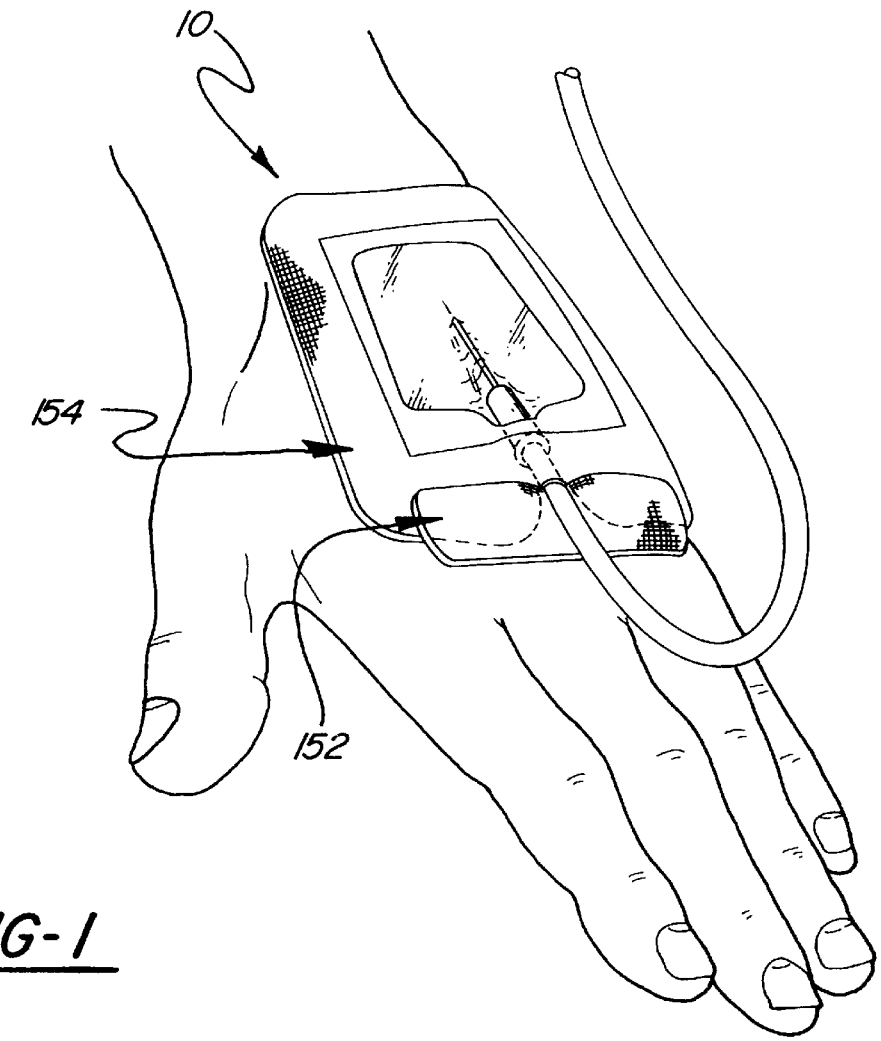
FIG. 1 is an environmental view of a self adherent window dressing constructed in accordance with the present invention adhered about an indwelling catheter access site in the hand of a patient.

Referring now to the drawings in detail, numeral 10 generally indicates a self adherent dermal wound window dressing used on a patient for the protection of a wound or indwelling catheter. As is hereinafter more fully described, the window dressing 10 permits continuous visual inspection of the site and combines a lint-free, highly-absorbent pad that reduces moisture accumulation that heretofore has obscured the site. Furthermore, the dressing 10 possesses high oxygen and moisture permeability, and provides an impermeable barrier to liquids and bacteria.

Figure 2:
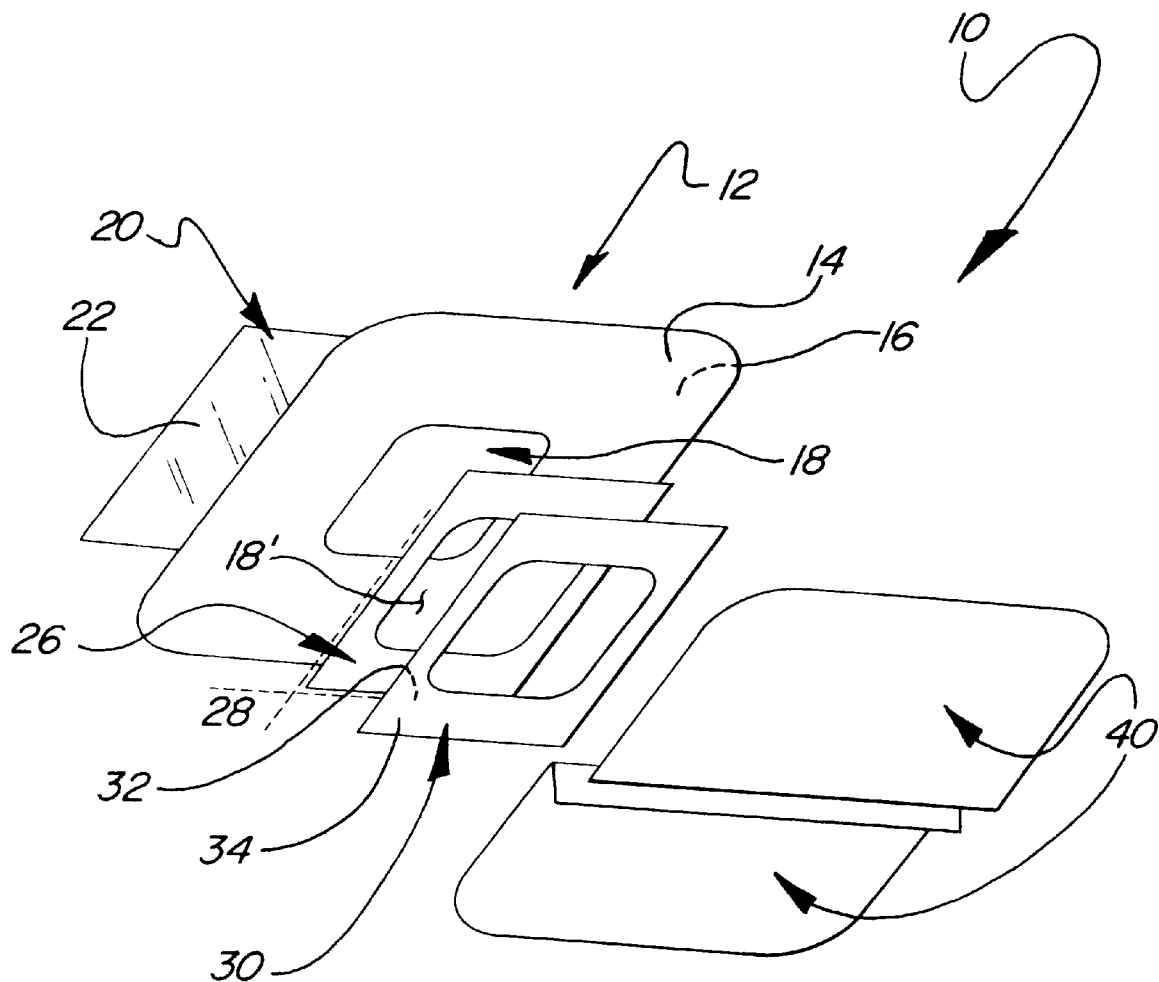
FIG. 2 is an exploded view of the self adherent window dressing of the invention illustrating its layered construction.

As disclosed in my co-pending patent application Ser. No. 08/918,211, filed Aug. 25, 1997, which is illustrated in FIG. 2 and hereby incorporated by reference, the window dressing 10 includes a breathable, non-woven fabric tape layer 12 having an adhesive side 14 and an opposite non-adhesive side 16. Preferably, the fabric layer adhesive side 14 is coated with a hypoallergenic adhesive that is non-sensitizing. The fabric tape layer 12 has an opening 18 therein to allow viewing of a catheter injection site, as illustrated in FIG. 1. A semipermeable transparent film layer 20 closes the opening 18 in the fabric tape layer 12. Preferably, the semipermeable transparent film layer 20 comprises a liquid impermeable, bacterial static polyurethane film. Preferably, the polyurethane film 20 is also gas and moisture vapor permeable, providing a high level of moisture vapor and gas (oxygen) exchange, for maintaining normal skin function.

The transparent film layer 20 has an adhesive side 22 coated with a medical grade adhesive and an opposite non-adhesive side. The film layer adhesive side 22 is adhered on the non-adhesive side 16 of the fabric layer 12 around the opening 18.

An absorbent fiber layer 26 having an opening 18', generally corresponding to the opening 18 in the fabric tape layer 12, is mounted on the adhesive side 14 of the fabric tape layer such that the openings 18,18' in the absorbent fiber and fabric tape layers are in alignment and the fabric tape layer extends beyond the periphery 28 of the absorbent fiber layer. Absorbent fiber layer 26 provides circumfluent moisture absorption around the opening 18 keeping the viewing area clear and dry. Absorbent fiber layer 26 also provides a cushion for the catheter. Preferably, the absorbent fiber layer 26 is a nonwoven fabric.

A non-adherent porous film layer 30 of a shape generally corresponding to the shape of the absorbent layer 26 and having an adhesive side 32 and an opposite non-adhesive side 34 is adhered to the absorbent fiber layer 26 by the adhesive side of the non-adherent porous film layer. The non-adherent porous film layer 30 can be a polyethylene film or other suitable material that will not stick to the site upon removal.

The window dressing 10 also includes a removable silicone-coated, or other non-stick paper 40 of a shape corresponding to the shape of said fabric tape layer 12. This paper 40 is disposed over the absorbent 26 and non-adherent porous film 30 layers against the adhesive side 14 of the fabric tape layer extending beyond the absorbent fiber layer periphery. Paper 40 may be of one piece or multiple piece construction and is removed to allow the adhesive side 14 of the fabric tape layer 12 to be adhered to a patient.

Figure 5:
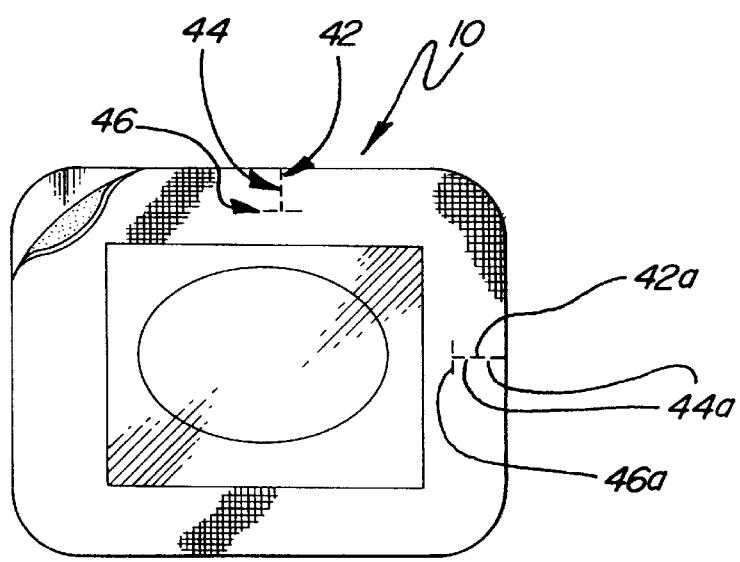
FIG. 5 is a plan view of a self adherent window dressing according to yet another embodiment of the invention.
Figure 3:
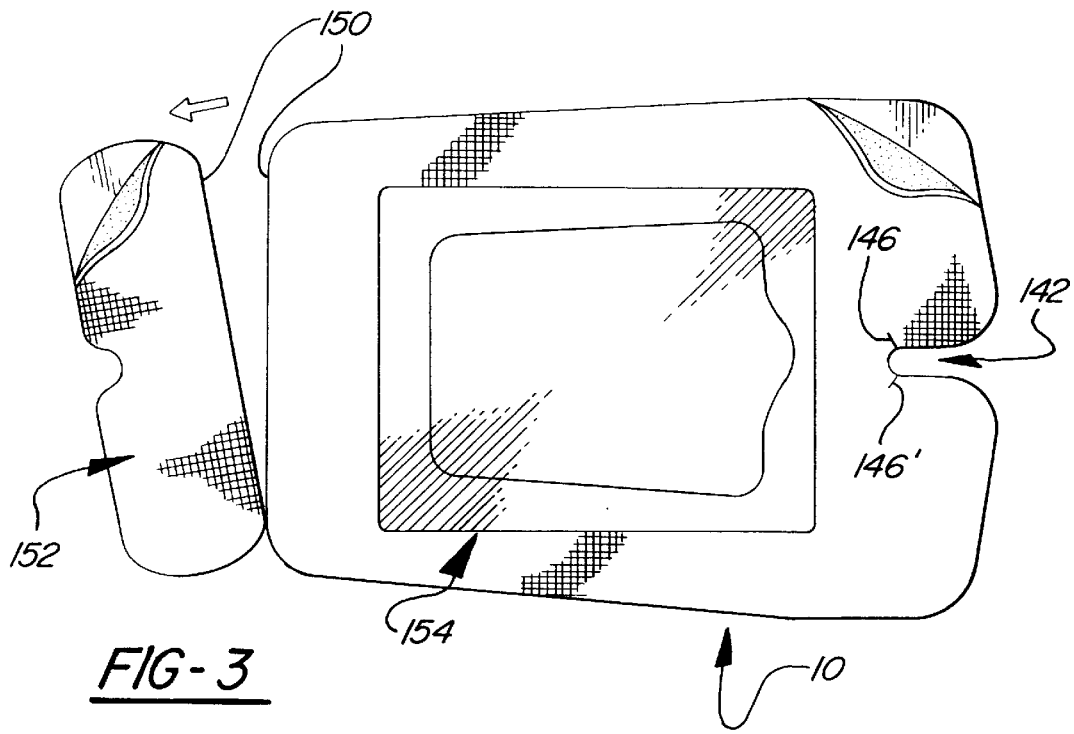
FIG. 3 is a plan view of a self adherent window dressing of the invention illustrating a separable portion and a dressing portion incorporating an overt notched shape which extends inwardly from the edge of the fabric tape layer.
Figure 4:
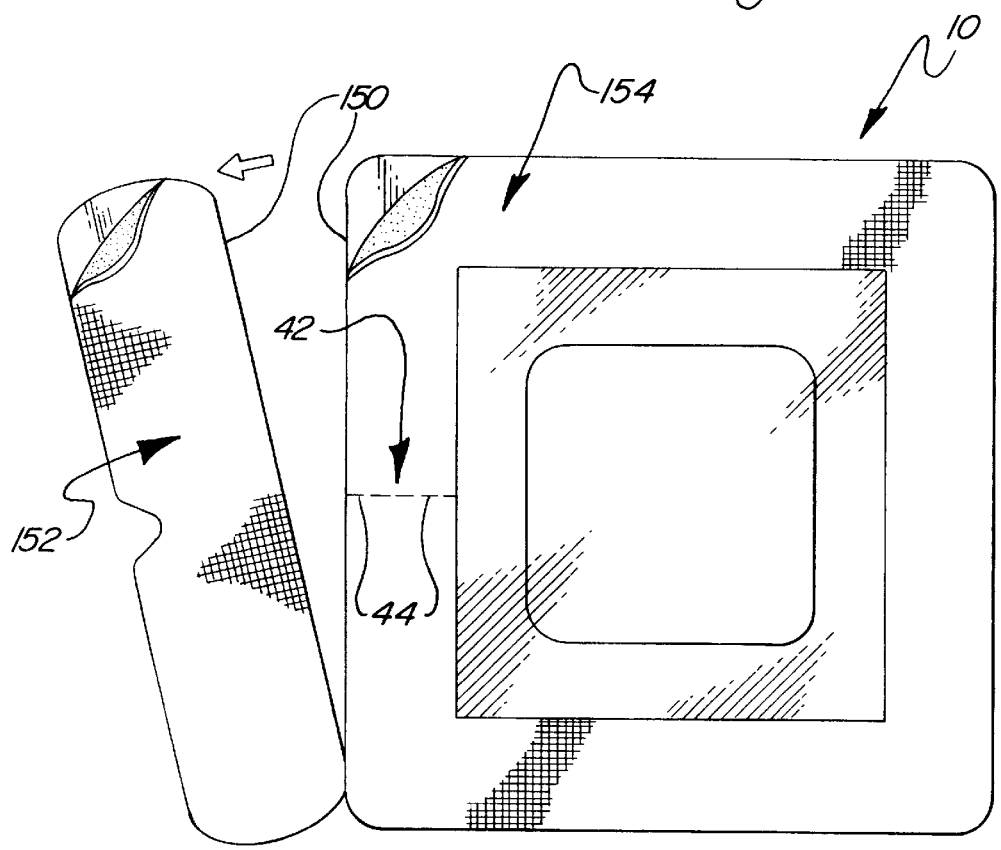
FIG. 4 is a plan view of a self adherent window dressing according to another embodiment of the invention incorporating a latent cut extending inwardly from the edge of the fabric tape layer and is interrupted by separable connecting portions which hold the edge of the fabric tape layer adjacent the cut together.

Referring now to FIGS. 3, 4 and 5, the window dressing includes a latent cut 42 in the fabric tape layer extending beyond the periphery of the absorbent fiber layer. Latent cut 42 receives a catheter tube extending from under the dressing and the fabric tape layer conformingly and occlusively seals the dermal wound window dressing from contamination around the catheter tube as hereinafter described.

In one embodiment of the invention, illustrated in FIGS. 4 and 5, the cut 42 extends inwardly from the edge of the fabric tape layer and is interrupted by connecting portions 44 which hold the edge of the fabric tape layer adjacent the cut, together. Upon application for use, the connecting portions 44 separate to allow the edge of the fabric tape layer to form an occlusive seal by stretching and conforming into the shape of an overt notch around the catheter tube extending from under the dressing.

As illustrated in FIG. 5, the latent cut feature is incorporated more than once into the edge of the fabric tape layer to accommodate more than one orientation of the dressing in application to the patient's skin forming an occlusive seal by stretching and conforming into the shape of a notch around the catheter tube extending from under the dressing. The latent cuts 42 and 42a terminate into perpendicularly extending cuts 46 and 46a and open to create an occlusive seal in their application and facilitate easy removal of the dressing from around the catheter tube.

As illustrated in the embodiment of FIG. 3, cut 142 is a generally U-shaped indentation extending inwardly from the edge of the fabric tape layer. A V-shaped cut can be substituted for the U-shaped cut 142. The window dressing, illustrated in FIG. 3, includes two spaced cuts 146, 146' extending inwardly from the indentation 142 facilitating conformability of the tape layer to surround the catheter.

With further reference to FIGS. 1, 3 and 4, the fabric tape layer extending beyond the absorbent fiber layer periphery includes a line of perforation 150 allowing a separable portion 152 of the fabric tape layer to be separated from a dressing portion 154 of the window dressing. Therein, one or both portions 152, 154 of the fabric tape layer include a latent cut extending inwardly from an edge thereof. These cuts are aligned when the dressing is applied, allowing for adhesive securement of the separable portion to the skin of a patient under a catheter tube as it emerges from underneath the dressing with the tube received by the cuts, and between the skin and dressing portion along the edges thereof in opposite directions from the tube exit location, as illustrated in FIG. 1.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A self adherent dermal wound window dressing for the protection of an indwelling catheter access site, and which provides the simultaneous absorption and continuous mitigation of moisture vapor, visualization of the skin or cannula exit point and mechanical securement of the indwelling catheter, the window dressing comprising:

a fabric tape layer having an adhesive side and an opposite non-adhesive side; said fabric tape layer having an opening therein to allow viewing therethough;

a semipermeable transparent film layer closing said opening in said fabric tape layer and having an adhesive side and an opposite non-adhesive side; said film layer adhesive side being adhered on the non-adhesive side of said fabric layer around said opening;

an absorbent fiber layer having an opening generally corresponding to said opening in said fabric tape layer, said fiber layer mounted on the adhesive side of said fabric tape layer such that said openings in said absorbent fiber and fabric tape layers are in alignment and said fabric tape layer extends beyond the periphery of said absorbent fiber layer;

a non-adherent porous film layer of a shape generally corresponding to the shape of said absorbent fiber layer having an adhesive side and an opposite non-adhesive side and adhered to said absorbent fiber layer by said adhesive side of said non-adherent porous film layer; and a latent cut in the fabric tape layer extending beyond the periphery of said absorbent fiber layer for receiving a catheter extending from under the dressing.

2. The window dressing of claim 1 wherein said latent cut extends inwardly from the edge of said fabric tape layer.

3. The window dressing of claim 2 wherein said latent cut is interrupted by connecting portions which hold the edge of said fabric tape layer adjacent said latent cut together and that separate to form an occlusive seal by stretching and conforming into the shape of a notch around the catheter when the dressing is applied.

4. The window dressing of claim 1 wherein said latent cut terminates in a perpendicularly extending cut facilitating conformability of said tape layer to surround the catheter.

5. The window dressing of claim 1 wherein said latent cut is an indentation extending inwardly from the edge of said fabric tape layer.

6. The window dressing of claim 5 including at least two spaced cuts extending inwardly from said indentation facilitating conformability of said tape layer to surround the catheter.

7. The window dressing of claim 6 wherein said indentation is generally V-shaped.

8. The window dressing of claim 6 wherein said indentation is generally U-shaped.

9. The window dressing of claim 6 wherein said fabric tape layer extending beyond said absorbent fiber layer periphery includes a line of perforation allowing a separable portion of said fabric tape layer to be separated from a dressing portion of said window dressing; and one or both portions of said fabric tape layer include a cut extending inwardly from an edge thereof that cooperates when applied to allow for adhesive securement of the separable portion to the skin of a patient under a catheter as it emerges from underneath the dressing with the tube received by said cuts, and between the skin and dressing portion along the edges thereof in opposite directions from the catheter exit location.

10. A self adherent dermal wound window dressing for the protection of an indwelling catheter access site, and which provides the simultaneous absorption and continuous mitigation of moisture vapor, visualization of the skin or cannula exit point and mechanical securement of the indwelling catheter, the window dressing comprising:

a fabric tape layer having an adhesive side coated with a hypoallergenic adhesive and an opposite non-adhesive side; said fabric tape layer having an opening therein to allow viewing therethrough;

a gas and moisture vapor permeable, liquid impermeable transparent film layer closing said opening in said fabric tape layer and having an adhesive side and an opposite non-adhesive side; said film layer adhesive side being adhered on the non-adhesive side of said fabric layer around said opening;

an absorbent, nonwoven fiber layer having an opening generally corresponding to said opening in said fabric tape layer, said fiber layer mounted on the adhesive side of said fabric tape layer such that said openings in said fiber and fabric tape layers are in alignment and said fabric tape layer extends beyond the periphery of said absorbent fiber layer;

a non-adherent porous film layer of a shape generally corresponding to the shape of said absorbent fiber layer having an adhesive side and an opposite non-adhesive side and adhered to said fiber layer by said adhesive side of said non-adherent porous film layer; and an overt notch formed by removal of a portion of the fabric tape layer extending beyond the periphery of said absorbent fiber layer for receiving a catheter tube extending from under the dressing.

11. The window dressing of claim 10 including at least two spaced cuts extending inwardly from said notch facilitating conformability of said tape layer to surround the catheter.

12. The window dressing of claim 11 wherein said notch is generally V-shaped.

13. The window dressing of claim 11 wherein said notch is generally U-shaped.

* * * * *